US00PP26602P3

(12) United States Plant Patent
Dobres

(10) Patent No.: US PP26,602 P3
(45) Date of Patent: Apr. 12, 2016

(54) ***VERONICA* PLANT NAMED 'NOVAVERBLU'**

(50) Latin Name: *Veronica spicata*
Varietal Denomination: Novaverblu

(71) Applicant: CP DELAWARE, INC., Wilmington, DE (US)

(72) Inventor: Michael S. Dobres, Philadelphia, PA (US)

(73) Assignee: CP DELAWARE, INC., Wilmington, DE (US)

( * ) Notice: Subject to any disclaimer, the term of this patent is extended or adjusted under 35 U.S.C. 154(b) by 147 days.

(21) Appl. No.: 13/998,816

(22) Filed: Dec. 11, 2013

(65) Prior Publication Data

US 2015/0163981 P1 Jun. 11, 2015

(51) Int. Cl.
*A01H 5/02* (2006.01)

(52) U.S. Cl.
USPC ..... Plt./251

(58) Field of Classification Search
USPC ..... Plt./251
See application file for complete search history.

(56) References Cited

PUBLICATIONS

Delaware Center for Horticulture 2013.*

* cited by examiner

*Primary Examiner* — Keith Robinson
(74) *Attorney, Agent, or Firm* — Buchanan, Ingersoll & Rooney PC

(57) ABSTRACT

The new plant resulted as a mutation of an open-pollinated seed of the 'Tickled Pink' cultivar (U.S. Plant Pat. No. 16,182) that was induced by exposure to gamma irradiation followed by selection. Attractive dark blue blossoms are formed in abundance with a propensity to rebloom following trimming in the absence of a vernalization requirement for flowering. A dense compact mounding growth habit is displayed. The stems that bear flowers are substantially upright. The plant is well suited for providing attractive ornamentation in the landscape.

2 Drawing Sheets

Botanical/commercial classification: *Veronica spicata/ Veronica* Plant.

Varietal denomination: cv. 'Novaverblu'.

SUMMARY OF THE INVENTION

The new plant of the present invention was derived from the 'Tickled Pink' cultivar (U.S. Plant Pat. No. 16,182) at West Grove, Pa., U.S.A. Open-pollinated seeds of the cultivar were collected from 'Tickled Pink' plants. The seeds were thereafter subjected on Sep. 22, 2009 to gamma irradiation in order to seek to induce various mutations. Following the gamma irradiation, the irradiated seeds were sown under greenhouse conditions during January 2010, and the resulting plants were found during the following summer and fall to differ from each other in many ways. A single plant of the present invention was selected and was preserved in view of its unique combination of attractive phenotypic characteristics. Had this plant not been created, identified and preserved it would have been lost to mankind.

It was found that the new *Veronica* plant of the present invention displays the following combination of characteristics:

(a) exhibits a dense compact mounding growth habit,
(b) forms upright stems in abundance,
(c) is lacking a vernalization requirement for flowering,
(d) forms in abundance attractive dark blue blossoms with a propensity to rebloom following trimming, and
(e) is well suited for providing attractive ornamentation in the landscape.

During observations to date, the plant has been found to be hardy in U.S.D.A. Hardiness Zone No. 6. No further definitive hardiness information has been obtained.

The new cultivar well meets the needs of the horticultural industry and can be grown to advantage as a perennial garden plant to provide colorful ornamentation. For instance, it can be grown in parks, gardens and residential settings.

Plants of the new cultivar can be readily distinguished from other *Veronica spicata* cultivars including its parent. More specifically, the 'Tickled Pink' cultivar forms bright pink blossoms instead of blossoms having the dark blue coloration of the new cultivar.

The new cultivar also can be readily distinguished from the 'Rotfuchs' cultivar (non-patented). Unlike the new cultivar, the 'Rotfuchs' cultivar forms dark pink blossoms, is less compact, and has been found to require vernalization during observations at West Grove, Pa., U.S.A.

The new cultivar further can be readily distinguished from the 'Royal Candles' cultivar (non-patented). Unlike the new cultivar, the 'Royal Candles' cultivar forms blue-purple blossoms, and commonly assumes a taller height.

The new cultivar further can be readily distinguished from the 'Novaverpin' cultivar (U.S. Plant Pat. No. 25,748, granted Jul. 28, 2015), the 'Novavermau' cultivar (U.S. Plant patent application No. 13/998,800, filed Dec. 18, 2013), and the 'Novaverlig' variety (U.S. Plant patent application Ser. No. 13/998,882, filed Dec. 18, 2013) by an inspection of the flowers. More specifically, the "Novaverpin' cultivar forms light pink flowers, the 'Novavermau' variety forms mauve flowers, and the 'Novaverlig' variety forms dissimilar dark blue flowers The rooting of cuttings has been used to asexually propagate the new cultivar at West Grove, Pa., U.S.A. It has been found that the characteristics of the new cultivar are stable and are reliably transmitted from one generation to another. Accordingly, the new cultivar can be asexually reproduced in a true-to-type manner.

The new cultivar of the present invention has been named 'Novaverblu', and will be maketed under the DARK BLUE MOODY BLUES Trademark.

BRIEF DESCRIPTION OF THE PHOTOGRAPHS

The accompanying photographs illustrate the new cultivar in color as nearly true as it is reasonably possible make the same in color illustrations of this nature. The plants were approximately two years of age and were being grown during May 2013 on their own roots at West Grove, Pa., U.S.A.

DETAILED BOTANICAL DESCRIPTION

Figure 1:
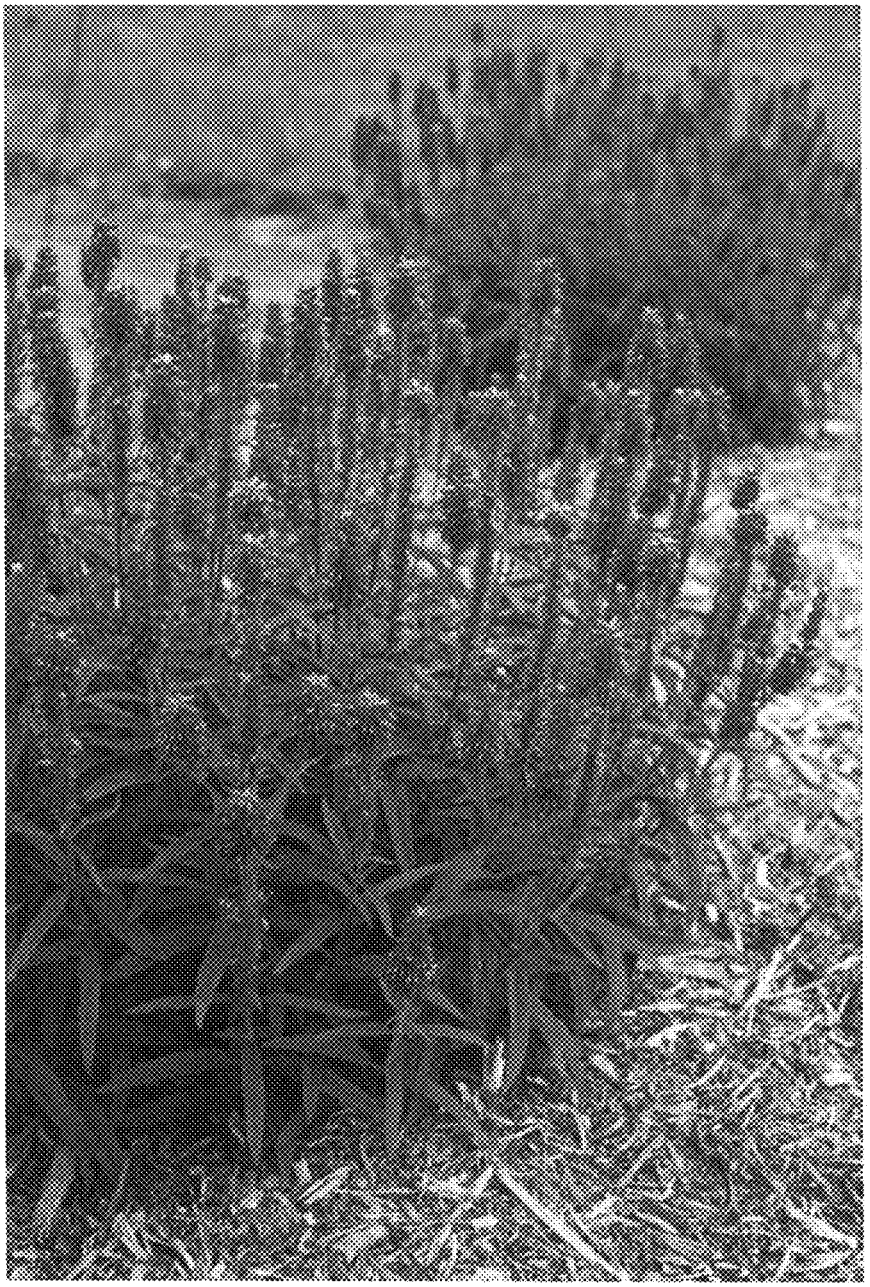
FIG. 1 illustrates primarily in the foreground a specimen of a typical mature flowering plant of the new cultivar while growing outdoors in the ground in full sun. The typical upright dense compact mounding growth habit is shown.
Figure 2:
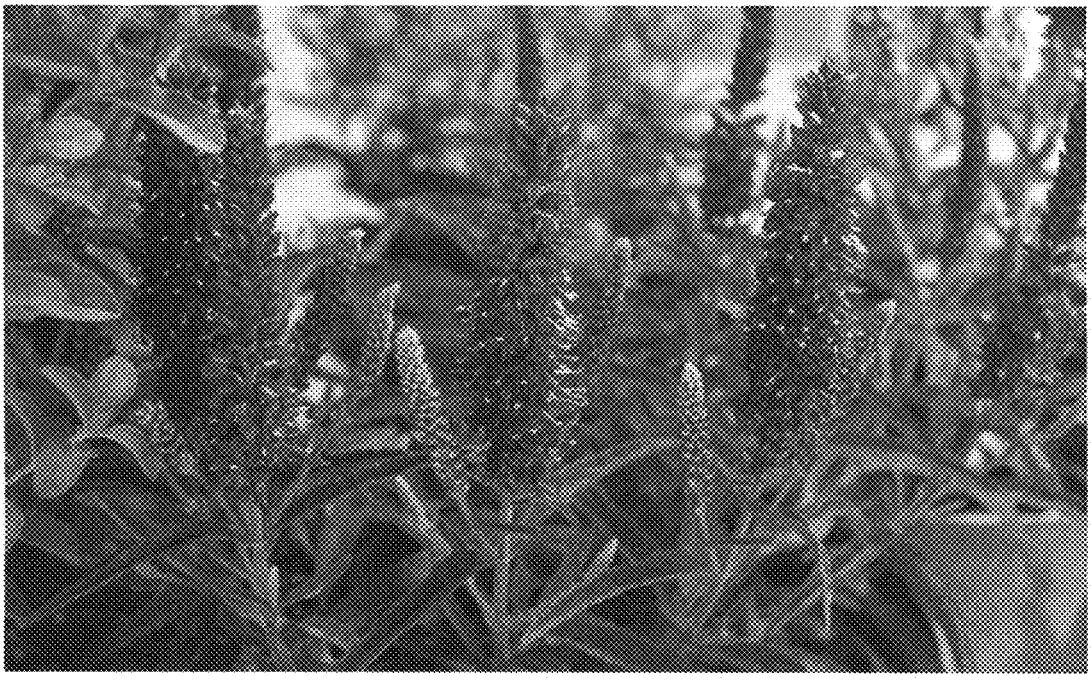
FIG. 2 illustrates a closer view of the dark blue flowers on upright stems of the new cultivar in various stages of development. The plant was being grown outdoors in a container.

The following is a detailed description while observing two-year-old plants of the new cultivar that were produced by the rooting of cuttings. Such plants were being grown in one-gallon containers under greenhouse conditions at West Grove, Pa., U.S.A. Also, size comparisons were made when grown outdoors in the ground. The chart used in the identification of color is The R.H.S. Colour Chart (1995 Edition) of The Royal Horticultural Society, London, England. Common color terms are to be accorded their customary dictionary significance.

Botanical classification: *Veronica spicata,* cv. 'Novaverblu'.

*Parent*.—Seedling of *Veronica spicata,* cv. 'Tickled Pink'.

*Plant type*.—Herbaceous perennial.

Plant:

*Growth habit*.—Dense compact and mounding.

*Height*.—Approximately 30 cm on average when grown in a container, and approximately 36 cm on average when grown in the ground.

*Spread*.—Approximately 44 cm on average when grown in a container, and approximately 46 cm on average when grown in the ground.

*Branching*.—Commonly approximately 7 to 12 lateral stems arise from a mat of congested basal stems.

*Branching angle*.—Commonly approximately 40 degrees.

*Branch length*.—Commonly approximately 16 cm on average.

*Branch diameter*.—Commonly approximately 1.5 mm on average.

*Branch shape*.—Substantially round in cross-section.

*Branch strength*.—Relatively strong.

*Branch color*.—Near Green Group 139C.

*Branch texture*.—Generally smooth with a finely pubescent surface.

*Internode length*.—Commonly approximately 1.7 cm.

*Roots*.—Fibrous network, near Orange-White Group 159D in coloration, with the rooting of cuttings commonly commencing in approximately 21 days on average, and a fully rooted plant commonly being produced in approximately 35 days on average.

Foliage:

*Arrangement*.—Opposite.

*Shape*.—Obovate to elliptic.

*Apex*.—Obtuse.

*Base*.—Acuminate.

*Length*.—Commonly approximately 7 cm on average for lower leaves, and approximately 3.5 cm on average for upper leaves.

*Width*.—Commonly approximately 1.6 cm on average for lower leaves and approximately 1 cm on average for upper leaves.

*Texture*.—On the upper surface sparsely pubescent, and on the under surface sparsely pubescent with moderate pubescence on the veins.

*Color*.—On the upper surface near Green Group 139A, and on the lower surface near Green Group 137C.

*Margins*.—Entire and somewhat crenate.

*Venation*.—Pinnate and near Yellow-Green Group 144A in coloration.

*Fragrance*.—None noticeable.

*Petiole*.—Commonly approximately 1 cm in length on average, approximately 2 mm in diameter on average, finely pubescent on both surfaces, and near Green Group 143B in coloration.

*Stipules*.—Absent.

Inflorescence:

*Season*.—Flowering commonly occurs May through July at West Grove, Pa., U.S.A.

*Reblooming*.—With a good propensity to rebloom following trimming.

*Type*.—Single arranged in upright racemes.

*Buds*.—Elongated ovoid, approximately 5 mm in length just before opening, approximately 2 mm in diameter, and near Violet-Blue Group 90D in coloration.

*Quantity*.—Free-flowering, commonly 1 or up to 6 arranged in a whorl, and commonly approximately 120 flowers per inflorescence.

*Racemes*.—Approximately 89 cm in length on average, and approximately 2 cm in width on average.

*Corolla diameter*.—Approximately 5 mm on average.

*Corolla length*.—Approximately 7 mm on average.

*Aspect*.—Commonly approximately 30 degrees prior to opening and substantially horizontal when fully open.

*Corolla configuration*.—Funnel-formed with petals fused into a tube towards the base.

*Petal number*.—Four.

*Petal tube*.—Approximately 2 mm in length on average, approximately 2 mm in width on average, glabrous in texture, and near Violet-Purple Group 91A in coloration.

*Petal lobes*.—Approximately 4 mm in length on average, approximately 5 mm in width on average, glabrous in texture on both surfaces, broadly linear in configuration, entire margins, rounded apex, and near Violet-Blue Group 90B on the upper surface and near Violet-Purple Group 90C on the under surface.

*Sepal arrangement*.—Four in number, fused at base.

*Sepal shape*.—Triangular-ovate.

*Sepal length*.—Approximately 2 mm on average.

*Sepal diameter*.—Approximately 1 mm on average.

*Sepal apex*.—Acute.

*Sepal margin*.—Entire.

*Sepal texture*.—Smooth on both surfaces.

*Sepal color*.—Near Yellow-Green Group 144A on the upper and under surfaces.
*Stamen number*.—Two.
*Anther shape*.—Ovoid.
*Anther length*.—Approximately 2 mm on average.
*Anther width*.—Approximately 1 mm on average.
*Anther color*.—Near Violet-Blue Group 91C.
*Filaments*.—Commonly approximately 6 mm in length on average, commonly less than 1 mm in diameter on average, and near Violet-Purple Group 91B in coloration.
*Pollen*.—Present in a moderate quantity, and near Greyed-Yellow Group 162D in coloration.
*Pistil number*.—One, with stigma and style not being readily distinguishable.
*Shape*.—Filiform.
*Color*.—Near Violet-Blue Group 93B.
*Length*.—Approximately 6 mm.
*Width*.—Commonly less than 1 mm.
*Ovary shape*.—Rounded.
*Ovary length*.—Approximately 1.5 mm on average.
*Ovary width*.—Approximately 1 mm on average.
*Ovary color*.—Near Green Group 142B.
*Seed number*.—Commonly 4 or less.
*Seed shape*.—Ovoid and commonly with flattening.
*Seed length*.—Approximately 1 mm on average.
*Seed width*.—Commonly less than 1 mm.
*Seed color*.—Greyed-Brown Group 199B.
*Fragrance*.—None observed.
*Flower longevity*.—Approximately 8 days on the plant.
*Peduncle length*.—Approximately 8 mm on average.
*Peduncle diameter*.—Substantially round and approximately 1 mm on average.
*Peduncle strength*.—Relatively strong.
*Peduncle texture*.—Finely pubsecent.
*Peduncle color*.—Near Green Group 139C.
*Pedicel length*.—Very short, and commonly approximately 0.05 mm.
*Pedicel width*.—Commonly less than 1 mm.
*Pedicel strength*.—Relatively strong.
*Pedicel texture*.—Smooth.
*Pedicel color*.—Near Green Group 143B.
*Fruit*.—Commonly approximately 3 mm in length on average, approximately 2.5 mm in diameter on average, smooth in texture, and near Yellow-Green Group 144A in coloration.
*Seeds*.—Commonly smooth in texture.

Disease resistance: No particular resistance to pathogens and pests common to *Veronica* plants has been encountered during observations to date.

Plants of the 'Novaverblu' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Veronica* plant having the following combination of characteristics:
(a) exhibits a dense compact mounding growth habit,
(b) forms upright stems in abundance,
(c) is lacking a vernalization requirement for flowering,
(d) forms in abundance attractive dark blue blossoms with a propensity to rebloom following trimming, and
(e) is well suited for providing attractive ornamentation in the landscape;
substantially as illustrated and described.

* * * * *